United States Patent
Demmer

(10) Patent No.: US 9,808,618 B2
(45) Date of Patent: **\*Nov. 7, 2017**

(54) DUAL CHAMBER INTRACARDIAC MEDICAL DEVICE

(71) Applicant: Medtronic, Inc., Minneapolis, MN (US)

(72) Inventor: Wade M Demmer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 83 days.

This patent is subject to a terminal disclaimer.

(21) Appl. No.: 14/694,775

(22) Filed: Apr. 23, 2015

(65) Prior Publication Data

US 2016/0310722 A1 Oct. 27, 2016

(51) Int. Cl.
| | |
|---|---|
| A61N 1/39 | (2006.01) |
| A61N 1/362 | (2006.01) |
| A61N 1/05 | (2006.01) |
| A61N 1/375 | (2006.01) |
| A61N 1/372 | (2006.01) |
| A61N 1/365 | (2006.01) |

(52) U.S. Cl.
CPC ............ *A61N 1/059* (2013.01); *A61N 1/362* (2013.01); *A61N 1/36592* (2013.01); *A61N 1/3756* (2013.01); *A61N 1/37205* (2013.01); *A61N 1/37217* (2013.01); *A61N 1/37264* (2013.01); *A61N 2001/37294* (2013.01)

(58) Field of Classification Search
CPC ..... A61N 1/362; A61N 1/3956; A61N 1/3968
See application file for complete search history.

(56) References Cited

U.S. PATENT DOCUMENTS

| | | | |
|---|---|---|---|
| 5,058,581 A | * | 10/1991 | Silvian ............... A61N 1/3727 128/903 |
| 5,174,288 A | * | 12/1992 | Bardy ................. A61N 1/0563 607/2 |
| 5,507,782 A | | 4/1996 | Kieval et al. |
| 5,683,432 A | | 11/1997 | Goedeke et al. |
| 5,683,447 A | | 11/1997 | Bush et al. |
| 5,716,391 A | | 2/1998 | Grandjean |
| 5,855,592 A | | 1/1999 | McGee et al. |
| 6,442,433 B1 | | 8/2002 | Linberg |
| 6,459,937 B1 | | 10/2002 | Morgan et al. |
| 8,204,595 B2 | | 6/2012 | Pianca et al. |
| 8,332,036 B2 | | 12/2012 | Hastings et al. |
| 8,433,409 B2 | | 4/2013 | Johnson et al. |

(Continued)

OTHER PUBLICATIONS (PCT/US2016/028291) PCT Notification of Transmittal of the International Search Report and the Written Opinion of the International Searching Authority, dated Aug. 16, 2016, 12 pages.

(Continued)

*Primary Examiner* — William Levicky

(57) ABSTRACT

An implantable pacemaker has a first housing and a second housing tethered to the first housing by an elongated electrical conductor. The elongated electrical conductor has a proximal end coupled to the first housing and a distal end coupled to the second housing and includes a signal line configured to carry an electrical signal between the first housing and the second housing.

23 Claims, 10 Drawing Sheets

(56) References Cited

U.S. PATENT DOCUMENTS

| | | |
|---|---|---|
| 8,457,742 B2 | 6/2013 | Jacobson |
| 8,527,068 B2 | 9/2013 | Ostroff |
| 8,532,785 B1 | 9/2013 | Crutchfield et al. |
| 8,541,131 B2 | 9/2013 | Lund et al. |
| 8,634,912 B2 | 1/2014 | Bornzin et al. |
| 8,670,842 B1 | 3/2014 | Bornzin et al. |
| 8,781,605 B2 | 7/2014 | Bornzin et al. |
| 2004/0147973 A1 | 7/2004 | Hauser |
| 2004/0220626 A1* | 11/2004 | Wagner .................. A61N 1/05 607/4 |
| 2005/0055056 A1* | 3/2005 | Olson ................. A61N 1/3622 607/5 |
| 2006/0105018 A1* | 5/2006 | Epstein .................. A61L 27/34 424/426 |
| 2006/0241705 A1* | 10/2006 | Neumann ............. A61N 1/368 607/9 |
| 2007/0270916 A1* | 11/2007 | Fischell .................. A61N 1/37 607/36 |
| 2008/0161865 A1* | 7/2008 | Hagen .................... A61N 1/05 607/2 |
| 2009/0082828 A1 | 3/2009 | Ostroff |
| 2009/0192555 A1* | 7/2009 | Schleicher ............ A61N 1/375 607/2 |
| 2010/0137927 A1 | 6/2010 | Tkebuchava |
| 2011/0319952 A1 | 12/2011 | Virag et al. |
| 2013/0035748 A1 | 2/2013 | Bonner et al. |
| 2013/0116529 A1 | 5/2013 | Min et al. |
| 2013/0116738 A1* | 5/2013 | Samade ............... A61N 1/3756 607/3 |
| 2013/0197661 A1* | 8/2013 | Schwab ................... A61F 2/04 623/23.64 |
| 2013/0289644 A1 | 10/2013 | Martinez et al. |
| 2013/0303872 A1 | 11/2013 | Taff et al. |
| 2013/0325081 A1 | 12/2013 | Karst et al. |
| 2014/0100627 A1 | 4/2014 | Min |
| 2014/0107723 A1 | 4/2014 | Hou et al. |
| 2014/0121720 A1 | 5/2014 | Bonner et al. |
| 2014/0172034 A1* | 6/2014 | Bornzin ................ A61N 1/375 607/17 |
| 2014/0180306 A1 | 6/2014 | Grubac et al. |
| 2014/0214105 A1* | 7/2014 | DeGroot ............. A61N 1/3956 607/5 |
| 2016/0059003 A1 | 3/2016 | Eggen et al. |

OTHER PUBLICATIONS

"Biomaterials/Tissue Interactions: Possible Solutions to Overcome Foreign Body Response" Morais, JM et al. AAPS J., Jun. 2010; 12(2) pp. 188-196. Available at http://www.ncbi.nlm.nih.gov/pmc/articles/PMC2844517/.
(PCT/US2016/029040) PCT Notification of Transmittal of the International Search Report and the Written Opinion of the International Searching Authority, dated Jul. 27, 2016, 12 pages.

\* cited by examiner

DUAL CHAMBER INTRACARDIAC MEDICAL DEVICE

CROSS-REFERENCE TO RELATED APPLICATION

The present application is related to commonly-assigned U.S. patent application Ser. No. 62/151,855 which is entitled DUAL CHAMBER INTRACARDIAC MEDICAL DEVICE, filed provisionally and concurrently herewith and incorporated herein by reference in its entirety.

TECHNICAL FIELD

The disclosure relates to an implantable wholly intracardiac medical device for delivering cardiac pacing and/or sensing cardiac signals.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one medical lead for positioning electrodes in one heart chamber, atrial or ventricular, or a dual chamber pacemaker coupled to two leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are wholly implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular pacing may adequately address some patient conditions, other conditions may require atrial and ventricular pacing, commonly referred to as a dual chamber pacing, in order to maintain a regular heart rhythm.

SUMMARY

In general, the disclosure is directed to an intracardiac dual chamber pacemaker. The pacemaker includes a first housing and a second housing tethered to the first housing by an electrical conductor. The first and second housings each include a pulse generator for delivering pacing pulses to spaced apart pacing sites of a patient's heart.

In one example, the disclosure provides an implantable pacemaker comprising a first housing enclosing a first pulse generator configured for delivering first pacing pulses to a first heart location via at least one first electrode carried by the first housing and a second housing enclosing a second pulse generator configured for delivering second pacing pulses to a second heart location spaced apart from the first heart location via at least one second electrode carried by the second housing. The pacemaker further includes an elongated electrical conductor having a proximal end and a distal end, the proximal end coupled to the first housing and the distal end coupled to the second housing to tether the first housing and the second housing together. The elongated electrical conductor includes a signal line configured to carry an electrical signal between the first housing and the second housing.

In another example, the disclosure provides a method performed by an implantable pacemaker comprising a first housing enclosing a first pulse generator, a second housing enclosing a second pulse generator. The first and second housings are tethered together by an elongated electrical conductor having a proximal end coupled to the first housing and a distal end coupled to the second housing. The method includes delivering first pacing pulses to a first heart location via at least one first electrode carried by the first housing, delivering second pacing pulses to a second heart location spaced apart from the first heart location via at least one second electrode carried by the second housing, and transferring a signal along a signal line extending through the elongated electrical conductor between the first housing and the second housing to enable coordinated delivery of the first pacing pulses and the second pacing pulses.

In another example, the disclosure provides a non-transitory, computer-readable storage medium comprising a set of instructions which, when executed by a control module of an implantable pacemaker, cause the pacemaker to deliver first pacing pulses to a first heart location by a first pulse generator enclosed in a first housing via at least one first electrode carried by the first housing, deliver second pacing pulses to a second heart location by a second pulse generator enclosed in a second housing via at least one second electrode carried by the second housing; and transfer a signal via an elongated electrical conductor extending from the first housing to the second housing to enable coordinated delivery of the first pacing pulses and the second pacing pulses.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below

DETAILED DESCRIPTION

Figure 1:
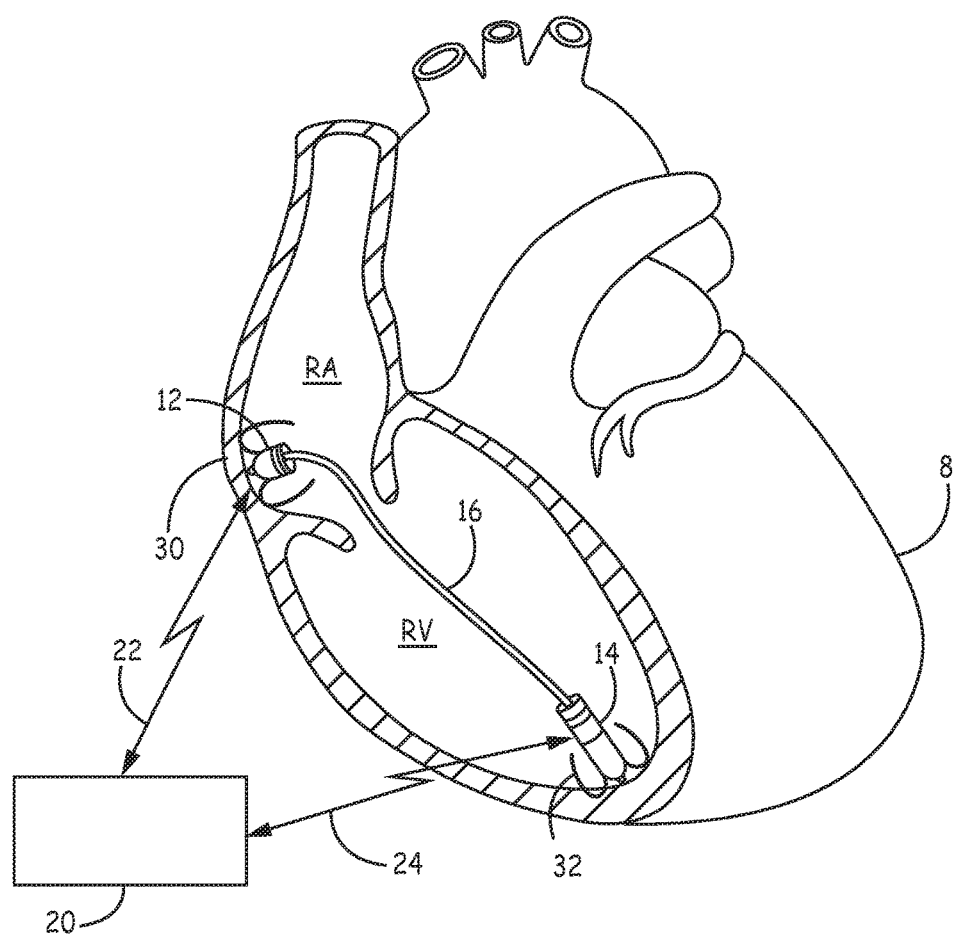
FIG. 1 is a conceptual diagram illustrating an intracardiac dual chamber pacemaker that may be used to sense cardiac electrical signals and provide therapy to a patient's heart.

FIG. 1 is a conceptual diagram illustrating an intracardiac dual chamber pacemaker 10 that may be used to sense cardiac electrical signals and provide therapy to a patient's heart 8. Pacemaker 10 is an elongated device that includes a right atrial (RA) intracardiac capsule 12 and a right ventricular (RV) intracardiac capsule 14. The capsules 12 and 14 are tethered together by electrical conductor 16. Pacemaker 10 is shown extending within the right atrium and the right ventricle of heart 8, but could be deployed to extend within the left atrium and the left ventricle.

In the example shown, RA capsule 12 is configured to sense RA cardiac signals and deliver RA pacing pulses via a pair of RA electrodes, which may be housing based electrodes incorporated along the housing of capsule 12. RV capsule 14 is configured to sense RV cardiac signals and deliver RV pacing pulses via a pair of RV electrodes, which may be housing based electrodes incorporated along the housing of capsule 14.

RA capsule 12 may include a fixation member 30 to retain capsule 12 in a desired location within the right atrium, and RV capsule 14 may include a fixation member 32 to retain capsule 14 in a desired location within the right ventricle. In the example of FIG. 1, capsule 12 is positioned along an endocardial wall of the RA, e.g., along the RA lateral wall, but could be positioned along the RA septum or other locations. Capsule 14 is positioned along an endocardial wall of the RV, e.g., near the RV apex. Pacemaker 10, however, is not limited to being positioned in the locations shown in the example of FIG. 1 and other positions and relative locations of capsules 12 and 14 with respect to one another and heart 8 are possible and will be selected based at least in part on particular patient need.

Capsules 12 and 14 are reduced in size compared to typical, subcutaneous-type pacemakers and may be generally cylindrical in shape to enable transvenous implantation of pacemaker 10 via a delivery catheter. The electrical conductor 16 may extend between any two locations of capsules 12 and 14 and is provided with a length that is adequate to reach between the two desired implant sites of capsules 12 and 14 without undue tension that would increase the likelihood of dislodgment or dislocation of either of the capsules 12 and 14. In various examples, without limitation, electrical conductor 16 may have a length between 5 cm and 25 cm in length.

In other examples, pacemaker 10 may be positioned along the outside of heart 8, including epicardial or pericardial locations. Capsule 12 may be positioned at one pacing site and capsule 14 positioned at a second pacing site spaced apart from the first pacing site, along the same or two different cardiac chambers to provide multi-site or dual chamber pacing therapy. For example, capsule 12 may be positioned outside along the right atrium or left atrium to provide respective right atrial or left atrial sensing and pacing. Capsule 14 may be positioned outside along the right ventricle or left ventricle to provide respective right ventricular or left ventricular pacing and sensing.

Capsules 12 and 14 each include pacing circuitry, e.g., a pacing pulse generator, for delivering electrical stimulation pulses, i.e., pacing pulses, to heart 8 via associated electrodes on the outer housings of capsules 12 and 14. The RA pacemaker 12 and the RV pacemaker 14 are configured to control the delivery of pacing pulses to the respective atrial and ventricular chambers in a manner that promotes coordinated dual chamber pacing. Examples of dual chamber pacing therapy delivered by separate atrial and ventricular intracardiac pacemakers are generally disclosed in commonly-assigned U.S. Pat. App. Publication No. 2014/0121720 (Bonner, et al.), incorporated herein by reference in its entirety. By including the tethering electrical conductor 16 between capsules 12 and 14, a signal may be transmitted between the capsules 12 and 14 to enable coordinated dual chamber pacing therapy at the two spaced apart pacing sites. The signal carried by tethering electrical conductor 16 may be a power transmission signal or a data communication signal in some examples. Frequent wireless telemetry communication signals are not required, which reduces the overall power capacity required by each of the separate capsules 12 and 14.

Pacemaker 10 is capable of bidirectional wireless communication with an external device 20. External device 20 may be a programmer used by a clinician or other user in a medical facility, a home monitor located in a patient's home, or a handheld device. Aspects of external device 20 may generally correspond to the external programming/monitoring unit disclosed in U.S. Pat. No. 5,507,782 (Kieval, et al.), hereby incorporated herein by reference in its entirety.

External device 20 may be configured to establish separate wireless radio frequency (RF) communication links 22 and 24 with separate implantable telemetry modules included in each of RA capsule 12 and RV capsule 14 to separately program and interrogate the individual RA capsule 12 and RV capsule 14 for respective RA pacing and sensing functions and RV sensing and pacing functions. In other examples, an implantable telemetry module is included in only one of RA capsule 12 and RV capsule 14 and a data line extends between the capsules 12 and 14 within electrical conductor 16 for transmitting data to and from external device 20 via a single implantable telemetry module.

An example RF telemetry communication system that may be implemented in external device 20 and pacemaker 10 is generally disclosed in U.S. Pat. No. 5,683,432 (Goedeke, et al.), hereby incorporated herein by reference in its entirety. Communication links 22 and 24 may be established using a radio frequency (RF) link, for example in the Medical Implant Communication Service (MICS) band, Medical Data Service (MEDS) band, BLUETOOTH® or Wi-Fi.

External device 20 may be capable of bi-directional communication with pacemaker 10 over a wide range of distances, e.g., up to approximately 10 meters. In other examples, telemetry communication may require the use of a programming head placed in proximity of the patient, e.g. against or within several centimeters of the patient's skin or clothing, to facilitate data transfer.

It is contemplated that external device 20 may be in wired or wireless connection to a communication network for transferring data to a remote database or computer to allow remote management of the patient. An example communication scheme that may be used for remotely programming pacemaker 10 using the techniques disclosed herein is generally disclosed in U.S. Pat. No. 6,442,433 (Linberg), incorporated herein by reference in their entirety.

External device 20 may be used for retrieving and sending data from pacemaker 10. Examples of retrieved data include physiological signals such as RA or RV EGM signals, therapy delivery data such as a history of pacing frequency, results of device diagnostic testing, current operating control parameters or other data stored by the pacemaker. Data sent to pacemaker 10 may include programmable control parameters used by the RA capsule 12 and RV capsule 14 to control sensing and pacing functions.

Both capsules 12 and 14 may include separate implantable telemetry modules configured to periodically "listen" for a valid "wake up" telemetry signal from external device 20 and power up to establish a communication link 22 or 24 in response to a valid RF telemetry signal (or go back to "sleep" if no valid telemetry signal is received). However, capsules 12 and 14 may not be configured to transmit a "wake up" signal to the other capsule 12 or 14 to initiate a communication session. In some cases, electrical conductor 16 includes a data line that enables data signals to be transmitted between RA capsule 12 and RV capsule 14. In other examples, electrical conductor 16 is solely a power transmission cable and does not include a data transmission line. In these instances, the capsules 12 and 14 may or may not be configured to communicate wirelessly with each other via the separate telemetry modules. For example, neither RA capsule 12 nor RV capsule 14 may be configured to initiate an RF communication session with the other capsule. In other cases, the two capsules 12 and 14 may be configured to communicate wirelessly with each other, but, in order to conserve battery life of the pacemaker 10, wireless telemetry communication between capsules 12 and 14 may be minimized.

Figure 2A:
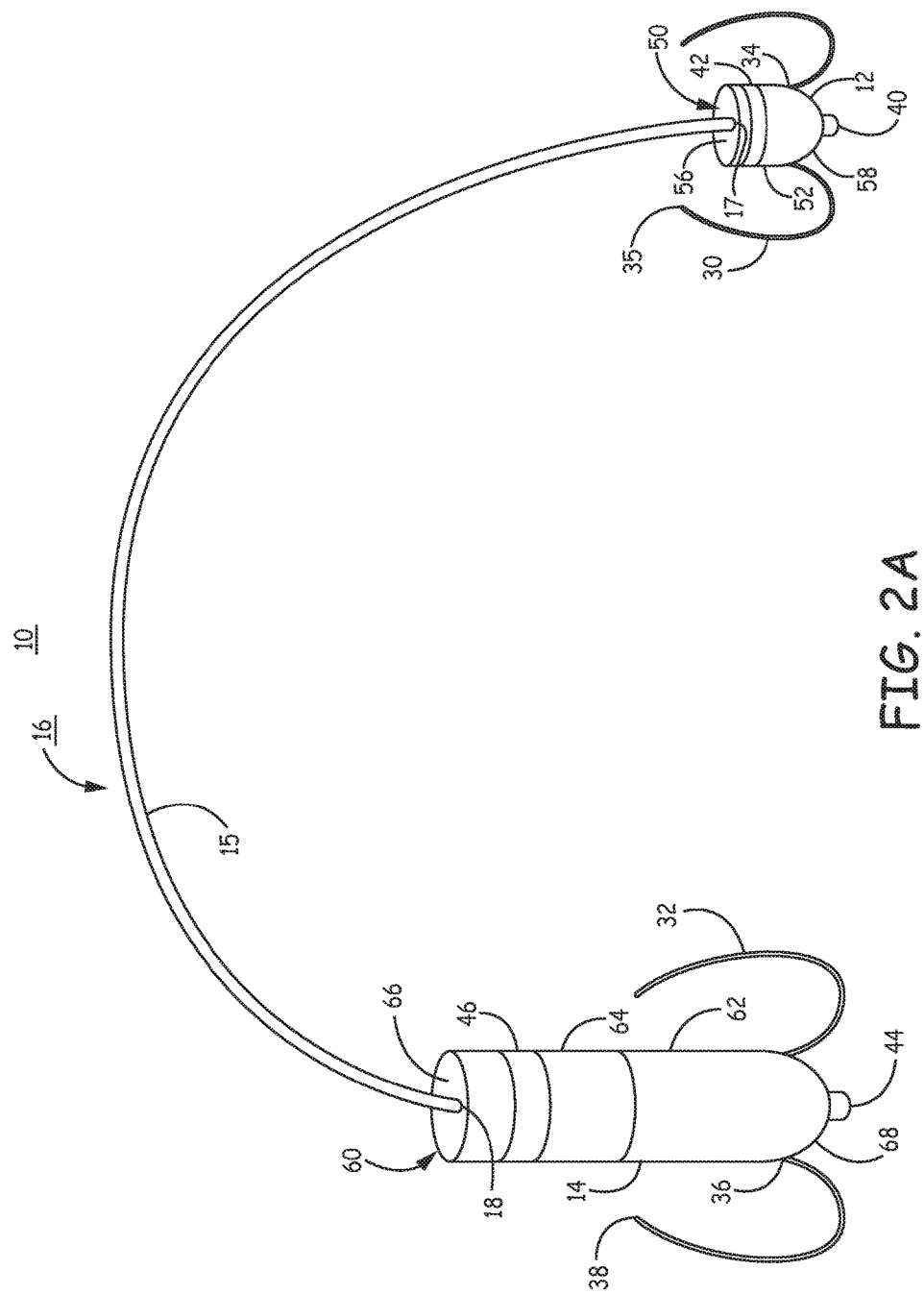
FIG. 2A is a conceptual diagram of the intracardiac pacemaker shown in FIG. 1.

FIG. 2 is a conceptual diagram of intracardiac pacemaker 10 shown in FIG. 1. Pacemaker 10 includes capsule housing 50 and capsule housing 60 tethered together by electrical conductor 16. Housing 50 is shown having a smaller outer dimension than housing 60. In some examples, housing 50 has the same or similar diameter but a shorter length than housing 60 as shown in FIG. 2. The relative lengths, outer diameters, and sizes of capsules 12 and 14 are not necessarily drawn to scale in FIG. 2 and may vary between embodiments. In other examples, housing 50 may have the same or similar length as housing 60 but a smaller outer diameter. In still other examples, housing 50 and housing 60 may have approximately the same outer dimensions or may differ in both length and outer diameter. Depending on the intended implant locations of capsules 12 and 14, the overall dimensions of housing 50 and 60 may be adapted accordingly.

Capsules 12 and 14 are generally cylindrical in shape to facilitate delivery of pacemaker 10 via a catheter or other generally tubular delivery tool. For example, capsule 14 may be positioned near a distal opening of a delivery catheter with electrical conductor 16 and capsule 12 extending within the catheter lumen in a proximal direction from the catheter distal opening. In this way, pacemaker 10 may be delivered by first releasing capsule 14 from the catheter distal opening at a first desired implant location, e.g., in or along the right ventricle. The delivery catheter may then be withdrawn to release electrical conductor 16 and position the distal opening of the delivery catheter at a second desired implant location. Capsule 12 may then be released at the second implant location, e.g., in the right atrium. It is recognized however, that capsules 12 and 14 may be provided with other outer geometries, such as generally prismatic shapes, spherical, etc.

In the illustrative embodiment of FIG. 1, capsule 12 is intended for RA implantation and is provided with a smaller length than capsule 14 intended for RV implantation. Housing 50 may include a control electronics subassembly 52, and housing 60 may include a control electronics subassembly 62 assembled with a battery subassembly 64. The battery subassembly 64 of capsule 14 may provide power to the both the control electronics subassembly 62 of capsule 14 and the control electronics assembly 52 of capsule 12 enabling the overall volume of housing 50 to be smaller in than the overall volume of housing 60. In this example, electrical conductor 60 includes an insulated power supply line and a ground wire extending from the battery subassembly 64 to the control subassembly 52 of capsule 12.

Capsule 12 has a proximal housing end 56 and a distal housing end 58. Proximal housing end 56 is shown as a substantially flat portion of housing 50 but may be a more rounded or substantially hemispherical proximal end. A proximal electrode 42 may be provided as a ring electrode along housing 50, near proximal end 56. Proximal electrode 42 may be an uninsulated portion of housing 50 or electrically coupled to housing 50 to serve as an anode return electrode of a bipolar pacing and sensing electrode pair including electrodes 40 and 42. Distal housing end 58 is defined by control electronics subassembly 52 and a tip electrode 40. Tip electrode 40 is provided as the cathode electrode for delivering pacing pulses and is coupled to a pulse generator enclosed in control electronics subassembly 52 in some examples. Tip electrode 40 may also be coupled to a sensing module enclosed in control electronics subassembly 52 for sensing cardiac electrical signals, i.e., EGM signals.

Capsule 14 has a proximal housing end 66 and a distal housing end 68. Proximal housing end 66 is shown as a substantially flat portion of housing 60 but may be a rounded or substantially hemispherical proximal end. A proximal electrode 46 may be provided as a ring electrode along housing 60, near proximal end 66. Proximal electrode 46 may be an uninsulated portion of housing 60 or electrically coupled to housing 60 to serve as an anode return electrode of a bipolar pacing and sensing electrode pair including electrodes 44 and 46. Distal housing end 68 is defined by control electronics subassembly 62 and a tip electrode 44. Tip electrode 44 is provided as the cathode electrode for delivering pacing pulses and sensing EGM signals and is coupled to a pulse generator and sensing module enclosed in control electronics subassembly 62.

An active or passive fixation member 30 and 32 may be provided near each of distal housing ends 58 and 68, respectively, to maintain a stable position of respective tip electrodes 40 and 44 at desired pacing and sensing sites, e.g., within the right atrium and within the right ventricle respectively. As used herein, the terms "active" and "passive" with reference to a fixation member are used to describe the mechanical fixation function of the fixation member. The term "active fixation" refers to fixation of the respective fixation member within tissue at the implant site by intentionally piercing, perforating or penetrating through a tissue surface by the fixation member at the time of implantation.

In contrast, "passive fixation" refers to fixation of the respective member at an in implant site that does not include intentionally piercing, perforating or penetrating through a tissue surface at the time of implantation. Rather, "passive fixation" involves positioning the fixation member alongside or adjacent to tissue at the implant site and relying on passive interaction or engagement between the passive fixation member and the adjacent tissue structure(s) to passively hold the fixation member in place. An active fixation member, therefore, includes a sharp or piercing tip that enables penetration into a tissue surface whereas a passive fixation member does not include a sharp or piercing tip and may include rounded or blunt tips that are not intended to be inserted into a tissue surface.

Each of fixation members 30 and 32 may include multiple fixation tines as shown in FIG. 2. For example each of fixation members 30 and 32 may include two, three, four, six or more fixation tines. The individual tines may extend in a generally distal direction with respect to housing distal ends 58 and 68 from a fixed tine end 34 or 36 coupled to distal housing end 58 or 68, then curve or bend laterally and proximally to extend a free, terminal tine end 35 or 36 in a substantially proximal direction with respect to distal housing end 58 or 68. The fixation members 30 and 32 may be active fixation members configured to pierce into endocardial tissue to hold the respective capsule 12 or 14 in a stable position. In this case, tine free ends 35 and 38 are pointed to pierce through the tissue at the implant site. In other examples, one or both of fixation members 30 and 32 may be a passive fixation member that passively interacts with tissue at the implant site, e.g., the atrial pectinate muscles or the ventricular trabeculae, respectively, to maintain a stable position of tip electrode 40 or 44. In this case, tine free ends 35 and 38 may be rounded or blunt.

In one example, capsule 14 is configured to have a greater fixation force than capsule 12. The fixation force is the force required to dislodge or retract the capsule 14 or 12 from its respective implant site, e.g. by pulling on respective proximal housing ends 66 or 56 or on electrical conductor 16. In this way, if heart growth, repetitive motion or other forces produce tension along electrical conductor 16 between capsules 12 and 14, capsule 12 will preferentially dislodge from its implant location before (or instead of) capsule 14, allowing capsule 14 to remain stably located at its implant site.

The capsule 12 or 14 considered to be more critical in delivering therapy to heart 8 may be provided with a greater fixation force. In some examples, the more critical capsule may be capsule 14 positioned in the right ventricle as shown in FIG. 1 for delivering RV pacing in a patient with AV block. In other examples, the more critical capsule may be capsule 12 positioned in the right atrium for delivering bradycardia pacing in a patient with intact AV conduction, where capsule 14 may provide occasional back-up ventricular pacing only or ventricular pacing during atrial tachyarrhythmia, for example.

A higher fixation force for one of capsules 12 or 14 compared to the other of capsules 12 and 14 may be achieved by configuring one of the fixation members 30 or 32 with a greater fixation force. The fixation member 30 or 32 having a greater fixation force may have, for example but not limited to, a greater length, thicker diameter, greater material stiffness, or greater number of tines than the other of fixation members 30 or 32. Additionally or alternatively, fixation members 30 and 32 may have different shapes such as a sharper curvature or bend of fixation member tines that results in a greater pulling force required to dislodge one of the fixation members 30 or 32 from tissue at its implant site compared to the force required to dislodge the other one of fixation members 30 and 32 from its implant site.

In other examples, one of fixation members 30 or 32 is provided as an active fixation member and the other of fixation members 30 or 32 is provided as a passive fixation member that is more easily dislodged from an implant location than the active fixation member. An active fixation member may include a piercing tip, helical screw, or one or more active fixation tines as generally disclosed in U.S. Patent Publication No. 2014/0180306 (Grubac, et al.), incorporated herein by reference in its entirety. For example distal fixation member 32 may be an active fixation member including multiple fixation tines which may be perforating nitinol wires and proximal fixation member 30 may be passive polymer tines that do not pierce into tissue. Fixation member 30 may include tines that extend at a straight angle from capsule 12 instead of curving as shown in FIG. 2.

The active fixation tines of distal fixation member 32 may be held in a substantially straight, distally-extended position within a delivery tool or catheter such that the free tine ends 38 pierce into tissue at the implant site upon deployment from the delivery tool. The fixation tines may resume the unextended, pre-formed curved position shown in FIG. 2 upon full deployment from the delivery tool, actively engaging tissue at the implant site by perforating through the tissue and capturing tissue within at least the curved portion of the tines as they resume the unextended position shown.

Fixation members 30 and 32 may be formed from a biocompatible polymer, e.g., polyurethane, silicone, polyethylene, or polyether ether ketone, or from a metal or metal alloy, e.g., stainless steel, titanium, platinum, iridium, tantalum, nickel or alloys thereof, or a coated metal. Fixation members 30 and/or 32 may include a shape memory material such as Nitinol to retain a pre-formed bend or curve that is straightened when pacemaker 10 is placed in a delivery catheter or tool and restored after pacemaker 10 is released from the delivery catheter or tool.

Capsules 12 and 14 are shown tethered together by electrical conductor 16 at their respective proximal housing ends 56 and 66. In other words, electrical conductor 16 extends from its proximal end 17 coupled to proximal housing end 56 of capsule 12 to its distal end 18 coupled to proximal housing end 66 of capsule 14. Electrical conductor 16 may be fixedly coupled to proximal housing ends 56 and 66 in a permanent, non-removable manner. In other examples, electrical conductor 16 may be removable by a user and re-attachable at one or both of proximal end 17 and distal end 18.

Electrical conductor 16 includes an electrically-insulating elongated body 15 that encloses one or more lumens through which electrically conductive wires, cables or traces extend between capsules 12 and 14 for carrying power and/or data communication signals between capsules 12 and 14. In some examples, electrical conductor 16 is provided for exclusively conducting power and/or communication signals between capsules 12 and 14. In other examples, electrical conductor 16 may include one or more electrodes exposed along elongated body 15 for use in sensing cardiac electrical signals and/or delivering cardiac pacing pulses to heart 8 generated by either of capsules 12 or 14.

Figure 2B:
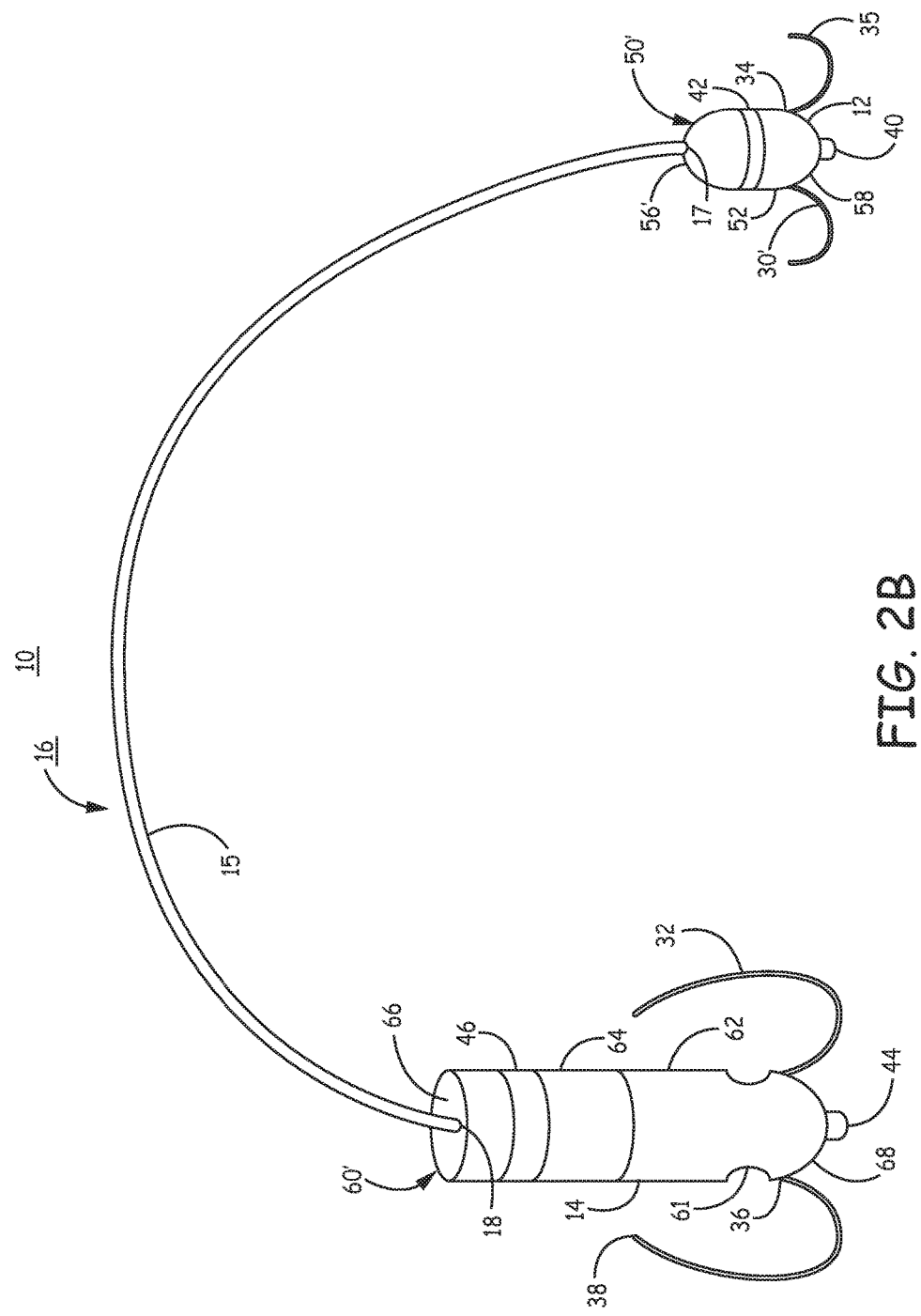
FIG. 2B is a conceptual diagram of an intracardiac pacemaker including one capsule having a greater fixation force.

FIG. 2B is a conceptual diagram of pacemaker 10 including one capsule 14 having a greater fixation force created by concave surface of housing 60'. In various examples, one of capsules 12 or 14 desired to have a greater fixation force may have a housing 50 or 60 that includes one or more concave surfaces that create a greater fixation force over time as tissue encapsulation of the capsule 12 or 14 takes place. Tissue encapsulation along or within a concave surface or annular feature of housing 50 or 60 creates a stronger resistance against retraction forces than tissue encapsulation around a laterally flat or convex surface.

In the example shown, housing 60' includes a circumferential concavity 61 along a portion of battery subassembly 64. In other examples, a concavity may be created along any portion of a longitudinal surface, e.g., the longitudinal sidewall extending between the proximal and distal ends 66 and 68 of housing 60,' to promote a narrowing or squeezing in of the tissue encapsulation along the capsule 14 that is substantially transverse to the direction of a longitudinal retraction force, e.g., along electrical conductor 16. Concavity 61 is shown near the housing distal end 68 which is expected to encapsulate earlier than housing proximal end 66 after implantation, thereby promoting early encapsulation of the concavity 61 and resistance to retraction forces. The growth of encapsulating tissue generally toward a central axis of housing 60', transverse to a longitudinal retraction force, will resist the retraction force. Concavity 61' is not necessarily drawn to scale with respect to housing 60' and may have a different radius defining the curvature of concavity 61 and/or a different depth from the exterior surface of longitudinal sidewall, relative to the overall diameter and length of housing 60', than as depicted in FIG. 2B.

Housing proximal end 66 is shown a substantially lateral flat surface that is transverse to the direction of a longitudinal retraction force and will further resist retraction and dislodgment of the housing 60'. Housing 50' includes a rounded convex or cone-shaped distal end 56' extending from substantially flat longitudinal sides. All exterior surfaces of housing 50' are substantially convex surfaces or longitudinally flat surfaces making the retraction force required to dislodge capsule 12 from tissue encapsulation at an implant site less than the retraction force required to dislodge capsule 14. The laterally flat distal end 66 and the concavity 61 of capsule 14 will increase the retraction force required to remove capsule 14 from an implant site compared to the retraction force required to remove capsule 12.

In some cases, all or a portion of housing 60' is covered by a coating that promotes tissue encapsulation or ingrowth for producing a greater fixation force of capsule 14. For example a generally non-smooth coating that creates pits, pores, ridges or bumps may promote a thicker tissue encapsulation and/or tissue ingrowth that result in a great fixation force. In one example, at least a portion of housing 60' is covered by DACRON® mesh or another synthetic porous material. A coating on all or a portion of housing 60' that is hydrophobic may promote macrophage adhesion and fusion leading to more rapid development of tissue encapsulation of the capsule 14.

Additionally or alternatively, capsule 12 may include a coating over all or a portion of housing 50' that has a surface chemistry and morphology that reduces encapsulation. For example, a coating on capsule 12 may be smoother, e.g., less porous, be a relatively more hydrophilic or neutral surface than the surface of housing 60', and/or include anti-inflammatory agents such that tissue encapsulation of capsule 12 is slower than or ultimately has a final encapsulation thickness that is less than tissue encapsulation of capsule 14. In various examples, with no limitation intended, a coating on housing 50' may include an anti-inflammatory drug such as dexamethasone, a synthetic coating such as polytetrafluoroethylene (PTFE), poly-lactic acid, polylactic coglycolic acid (PLGA), 2-hydroxyethyl methacrylate, polyethylene glycol, polyvinyl alcohol, or a phospholipid-containing material that reduces adhesion of inflammatory cells to housing 50'.

In FIG. 2B, capsule 12 is shown having a fixation member 30' with shorter fixation tines that will reduce the fixation force of capsule 12 relative to the longer fixation member tines of fixation member 32. Accordingly, greater fixation force of one capsule 14 relative to the other capsule 12 may be provided by including a concavity 61 of housing 60', an outer surface geometry and/or surface chemistry that promotes faster tissue encapsulation than the outer surface of housing 50', and/or a fixation member 32 that produces greater fixation force than fixation member 30'.

Figure 3:
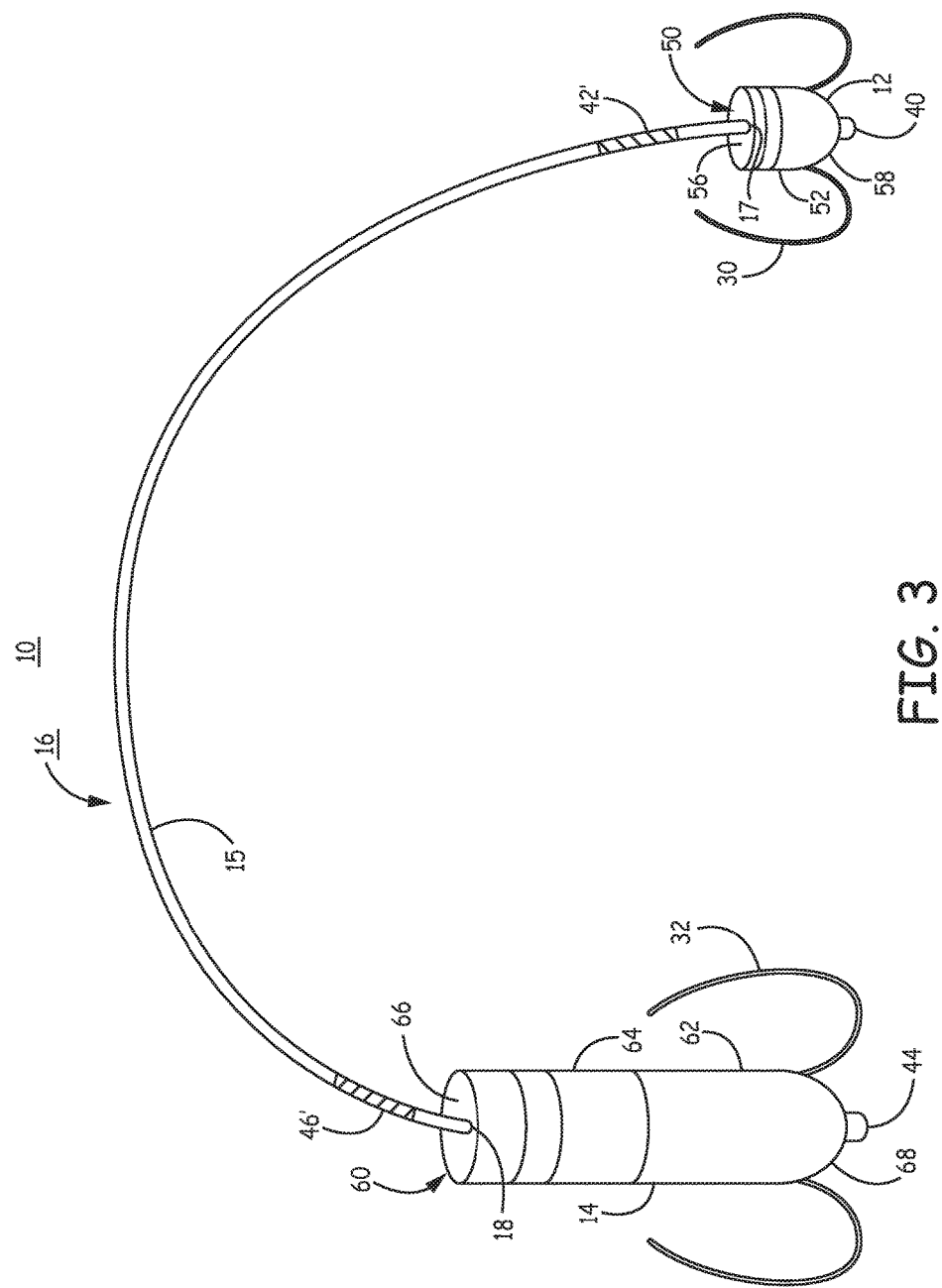
FIG. 3 is a conceptual diagram of the pacemaker shown in FIG. 1 including pace/sense electrodes along an electrical conductor that tethers the separate housings of the pacemaker.

FIG. 3 is a conceptual diagram of pacemaker 10 including pace/sense electrodes along electrical conductor 16. In some examples, as shown in FIG. 3, one or more ring electrodes 42' and 46' may be located along electrical conductor 16. Electrode 42' is positioned proximate to proximal housing end 56 to form a bipolar pair with tip electrode 40. Electrode 46' is shown proximate to proximal housing end 66 to form a bipolar pair with tip electrode 44. Instead of ring electrodes 42 and 46 along housings 50 and 60 as shown in FIG. 2, the ring electrodes 42' and 46' are each electrically coupled to the respective proximate housing 50 or 60 to provide a return anode for bipolar pacing and/or bipolar sensing with respective tip electrodes 40 and 44.

In other examples, electrodes 42' and 46' may be provided in addition to housing based ring electrodes 42 and 46 to provide multiple, different bipolar electrode combinations with respective pacing cathode electrodes 40 or 44 for sensing and pacing in a respective heart chamber. In still other examples, one anode electrode 42' may be provided along electrical conductor 16 and coupled to housing 50 of capsule 12, which may have a shorter length than capsule 14, and the other anode electrode 46 may be a housing-based electrode as shown in FIG. 2. An electrode 42' along electrical conductor 16 enables greater electrode spacing between cathode tip electrode 40 and anode electrode 42' than a housing based anode 42. Greater electrode spacing may be desired for some sensing applications.

Electrodes 40, 42, 42', 44, 46 and 46' shown in FIGS. 2 and 3 may be, without limitation, titanium, platinum, iridium or alloys thereof and may include low polarizing coatings, such as titanium nitride, iridium oxide, ruthenium oxide, platinum black, among others. Electrodes 40, 42, 44 and 46 may be positioned at locations along pacemaker housings 50 and 60 other than the locations shown.

Each of housings 50 and 60 may be formed from a biocompatible material, such as a stainless steel or titanium alloy. In some examples, the housings 50 and 60 include an insulating coating. Examples of insulating coatings include parylene, urethane, PEEK, or polyimide among others. The entirety of the housings 50 and 60 may be insulated, but only electrodes 40, 42, 44 and 46 uninsulated. In other examples, the entirety of the housing 50 or 60 may function as an electrode, insulated from tip electrodes 40 and 44, instead of providing a localized anode electrode 42 or 46.

Control electronics subassemblies 52 and 62 may each house the electronics for sensing cardiac signals and producing pacing pulses in the respective heart chambers in which the separate capsules 50 and 60 are implanted. As indicated above, housing 60 further includes a battery subassembly 64, which provides power to control electronics subassembly 62 and to control electronics subassembly 52 via electrical conductor 16. Battery subassembly 64 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Figure 4:
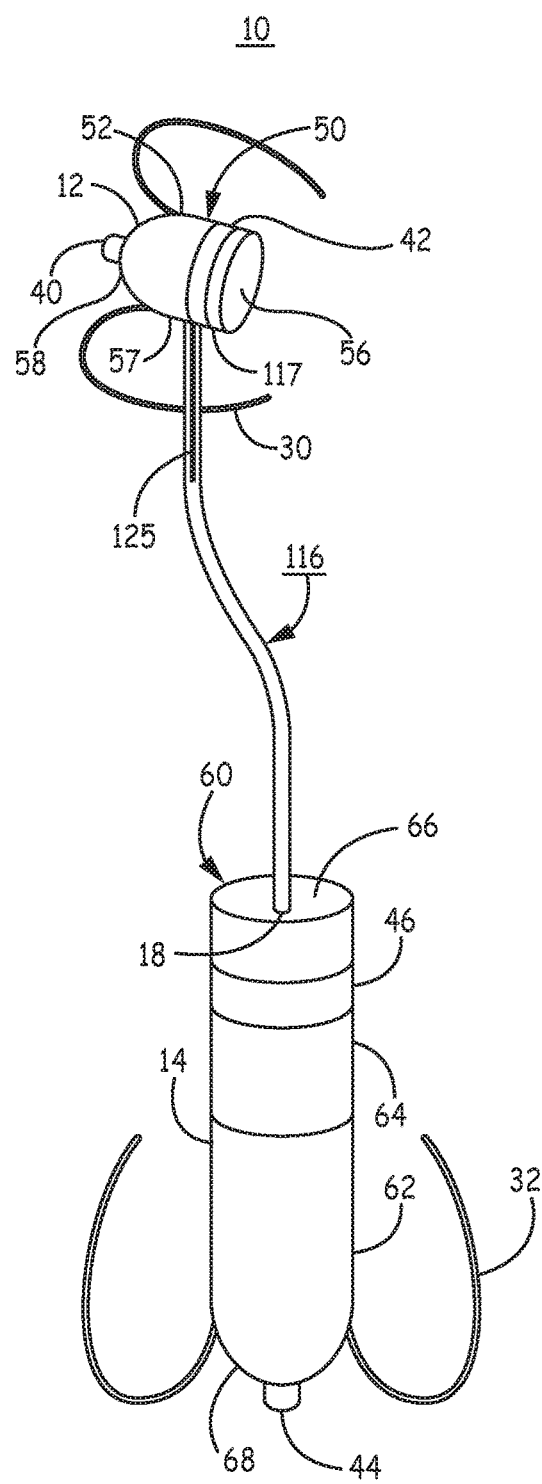
FIG. 4 is a conceptual diagram of an alternative arrangement of the pacemaker of FIG. 1.

FIG. 4 is a conceptual diagram of an alternative arrangement of pacemaker 10. In this example, the proximal end 117 of electrical conductor 116 is coupled to a lateral side 57 of capsule 12 that extends between proximal housing end 56 and distal housing end 58. Electrical conductor distal end 118 is shown coupled to proximal housing end 66 of capsule 14. In some examples, a side connection of electrical conductor 116 to one or both of the capsules 12 and 14 may alleviate tension on electrical conductor 116 after implantation and/or facilitate positioning of the capsules 12 and 14 at desired implant positions. The particular locations at which electrical conductor 16/116 is coupled to the capsules 12 and 14 of pacemaker 10 may vary between embodiments according to the requirements of a particular implanted configuration.

In the example of FIG. 4, a telemetry antenna 125 is shown extending along electrical conductor 116. Antenna 125 is coupled to a telemetry module enclosed by housing 50. When a telemetry module is included in either of capsules 12 or 14, the overall small size of capsules 12 and 14 limits antenna length for wireless telemetry communication with external device 20. An antenna 125 may extend from one or both housings 50 and 60 along electrical conductor 116. The antenna 125 is coupled to a telemetry module enclosed within the respective housing 50 or 60 using any necessary feedthrough to carry signals cross the housing.

Figure 5A:
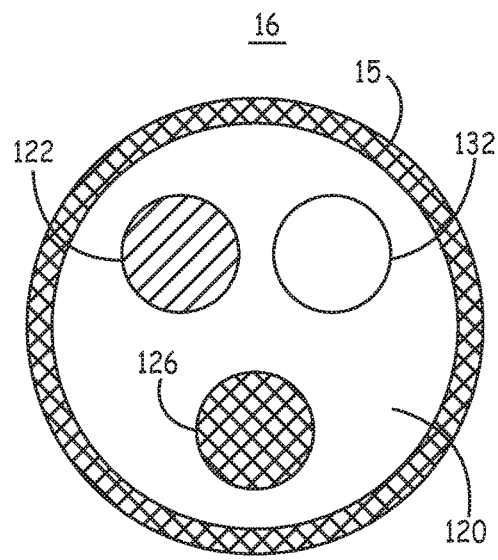
FIGS. 5A and 5B are exemplary sectional views of the tethering electrical conductor of the pacemaker of FIG. 1.

FIG. 5A is a sectional view of electrical conductor 16 according to one example. Electrical conductor 16 includes an elongated lead body 15 formed of an electrically insulating material, e.g., polyurethane, silicone, polyethylene or other flexible, biocompatible material. Lead body 15 may include a central open lumen 120 through which at least one insulated, electrically conductive wire or cable extends from the proximal end 17 to the distal end 18 of electrical conductor 16 for transmitting communication signals and/or power between capsules 12 and 14.

In the example shown, a data communication line 122 is provided for transmitted data signals between control electronics subassemblies 52 and 62 of capsules 12 and 14. Communication signals transmitted by data communication line 122, also referred to herein as "data line" 122, may include pace delivery signals and sensed event signals. For example, when capsule 14 is positioned in the right ventricle, a pace delivery signal may be transmitted to capsule 12, positioned in the right atrium, each time a right ventricular pacing pulse is delivered by capsule 14. Each time an R-wave is sensed by capsule 14, an R-wave sense signal may be transmitted from capsule 14 to capsule 12 via data line 122. Likewise, each time an atrial pacing pulse is delivered by RA capsule 12, a pacing delivery signal may be transmitted from capsule 12 to capsule 14. Each time a P-wave is sensed by RA capsule 12, a P-wave sense signal may be transmitted from capsule 12 to capsule 14. In this way, a control module included in each of the control electronics subassemblies 52 and 62 is notified when the other capsule is delivering a pacing pulse or sensing cardiac events such that the control modules can operate cooperatively in delivering dual chamber cardiac pacing or other pacing therapies.

An insulated power line 126 is also shown extending through lumen 120. Power line 126 may be included in electrical conductor 16 if one capsule, e.g., capsule 12, is not provided with its own power supply, and both capsules 12 and 14 are powered by a single source, e.g., battery subassembly 64 of capsule 14. Power line 126 provides a V+ power signal from battery subassembly 64 of capsule 14 to the control electronics subassembly 52 of capsule 12 in the example shown in FIG. 2. A ground line 132 may be included in some examples but may be optional since the housings 50 and 60 each provide a local ground connection for control electronics subassemblies 52 and 62, respectively. If the V+ power line 126 is present, ground line 132 may be desirable, however, to provide a circuit return path that is not through the patient's body.

In various examples, electrical conductor 16 may include only one signal line, e.g., data line 122. In other examples, electrical conductor 16 includes only V+ power line 126 and ground line 132. The number of electrical feedthroughs available for providing electrical coupling across housings 50 and 60 to signal lines included in electrical conductor 16 may be limited due to the overall size of housings 50 and 60. For example, a maximum of three electrical feedthroughs may be available to provide connection to a V+ power line 126, one data line 122, and one ground line 132.

The one data communication line 122 may be used in a half-duplex communication protocol for sending signals from capsule 12 to capsule 14 and from capsule 14 to capsule 12 in a non-interfering matter. A single bit digital communication signal may be transmitted via data line 122 for indicating when a pace or sense event occurs in a heart chamber to the capsule located in the other chamber. In other examples, communication may be "one-way" using a single data line 122. In other examples, data line 122 may include a multi-bit data bus for transmitting data between capsules 12 and 14.

As described in conjunction with FIG. 4 above, electrical conductor 16 may include an antenna 125 (not shown in FIG. 5A) extending along a portion of the lumen 120 from a respective housing 50 or 60 in some examples.

The lead body 15 is shown as a single lumen body in FIG. 5, but may be a multi-lumen body in other examples. A separate data communication line, power supply line and ground line may extend through multiple, isolated lumens from proximal end 17 to distal end 18 of electrical conductor 16. In some examples, electrical conductor 16 includes at least power line 126 for transferring a power signal or at least data line 122 for transferring a data communication signal so that the power signal or the data communication signal is carried between the proximal end 17 and the distal end 18 of the electrical conductor 16, between housings 50 and 60, to thereby enable pulse generators enclosed by each of the separate housings to operate in a coordinated manner for delivering dual chamber or multi-site pacing to heart 8.

Figure 5B:
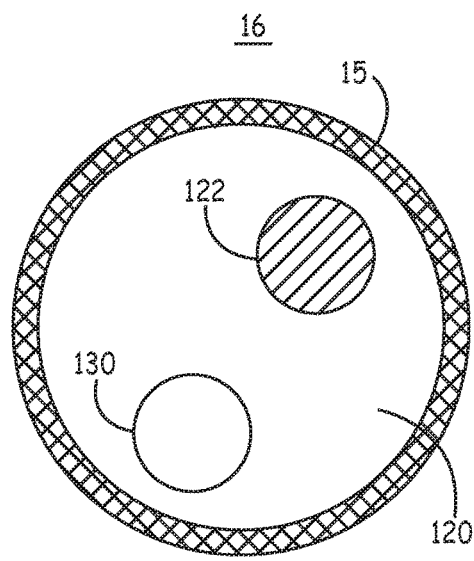

FIG. 5B is a sectional view of electrical conductor 16 according to an alternative example. In examples that include an anode electrode along electrical conductor 16, e.g., as shown in FIG. 3, an electrode lead conductor 130 extends through a portion of lumen 120, from the electrode 42' or 46' to the respective housing 50 or 60 to provide a return circuit path. In this example, electrical conductor also includes a communication data line 122 but does not provide power transmission between the two capsules 12 and 14.

Figure 6:
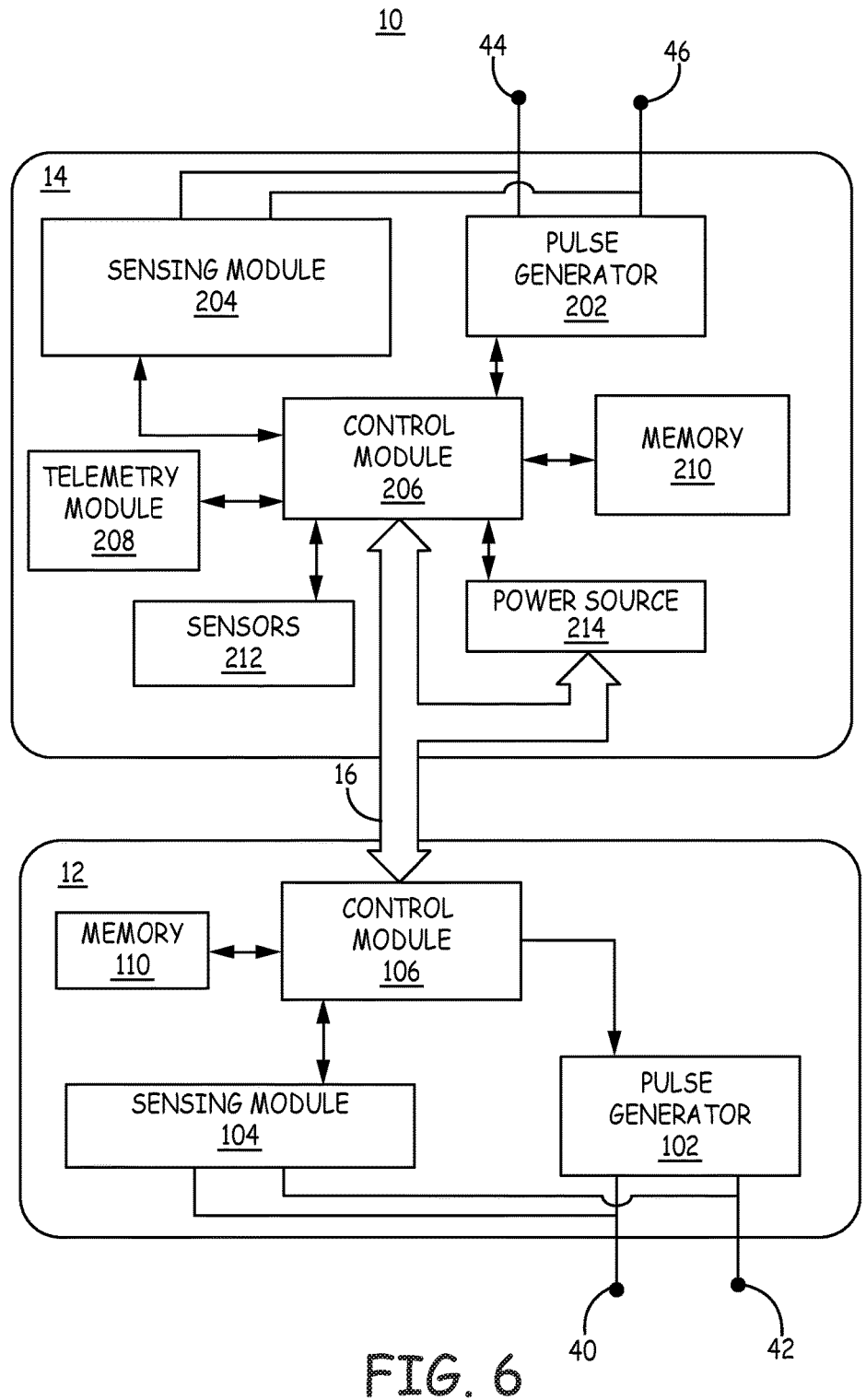
FIG. 6 is a functional block diagram of the pacemaker of FIG. 1 according to one example.

FIG. 6 is a functional block diagram of pacemaker 10 according to one example. RA capsule 12 includes a pulse generator 102, sensing module 104, control module 106, and memory 110 all enclosed in the housing 50 of control electronics subassembly 52. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. The functions attributed to a given capsule 12 or 14 herein may be embodied as one or more processors, controllers, hardware, firmware, software, or any combination thereof.

Pulse generator 102 generates electrical stimulation pulses that are delivered to heart tissue via electrodes 40 and 42 under the control of control module 106. Sensing module 104 receives cardiac signals developed across electrodes 40 and 42 for sensing cardiac events, e.g., P-waves in the right atrium. Sensing module 104 passes sensed event signals to control module 106. For example, sensing module 104 may be configured to sense P-waves in response to the EGM signal received from electrodes 40 and 42 crossing an auto-adjusting P-wave sensing threshold. Control module 106 controls pulse generator 102 to deliver RA pacing pulses as needed to maintain a desired heart rhythm according to a programmed pacing mode and other pacing control parameters.

Pacing control parameters and other operational control parameters may be stored in memory 110 for access by control module 106. In other examples, memory 110 is not included in capsule 12. Memory 210 included in RV capsule 210 may be used to store RA pacing and sensing control parameters accessible via electrical conductor 16 by control module 106.

Programmable control parameters used by control module 106 to control pacing and sensing functions may be received by telemetry module 208 of RV capsule 14, transmitted to capsule 12 via data communication lines in electrical conductor 16, and stored in memory 110. RA capsule 12 may not include a separate telemetry module in some examples for transmitting data to/from external device 20. Telemetry communication with external device 20 is performed by telemetry module 208 via electrical conductor 16.

RV capsule 14 includes pulse generator 202, sensing module 204, control module 206, memory 210, telemetry module 208 and a power source 214. Pulse generator 202 generates electrical stimulation pulses that are delivered to heart tissue via electrodes 44 and 46. Pulse generators 102 and 202 may include one or more capacitors and a charging circuit to charge the capacitor(s) to a programmed pacing pulse voltage. At appropriate times, e.g., as controlled by a pacing escape interval timer included in a pace timing and control circuit in control module 106 or 206, respectively, the capacitor is coupled to pacing electrodes 40, 42 or 44, 46, respectively, to discharge the capacitor voltage and thereby deliver the pacing pulse. Pacing circuitry generally disclosed in the above-incorporated U.S. Pat. No. 5,507,782 (Kieval, et al.) and in commonly assigned U.S. Pat. No. 8,532,785 (Crutchfield, et al.), incorporated herein by reference in its entirety, may be implemented in pacemaker 10 for charging a pacing capacitor to a predetermined pacing pulse amplitude under the control of control modules 106 or 206 and delivering a pacing pulse by the respective pacemaker capsule 12 or 14.

Sensing module 204 receives a cardiac EGM signal developed across electrodes 44 and 46 for sensing cardiac events, e.g., R-waves. Sensing module 204 passes sensed event signals to control module 206. For example, sensing module 204 may be configured to sense R-waves in response to the EGM signal received from electrodes 44 and 45 crossing an auto-adjusting R-wave sensing threshold. Sensing modules 104 and 204 may each include a bandpass filter, which may be an adjustable filter, having a center frequency and passband selected to filter non-cardiac signals and improve the signal-to-noise ratio for sensing intrinsic cardiac events.

Sensing modules 104 and 204 may each include a digital convertor that converts the EGM signal received across respective electrodes 40, 42 and 44, 46 to a multi-bit digital signal. Control modules 106 and 206 may receive the multi-bit digital signal from respective sensing module 104 or 204 and analyze the digital signal for use in detecting cardiac events and controlling pulse generators 102 and 202 to deliver appropriate therapy.

Memory 110 and memory 210 may each include computer-readable instructions that, when executed by respective control modules 106 and 206, cause respective RA capsule 12 or RV capsule 14 to perform various functions attributed throughout this disclosure to pacemaker 10. The computer-readable instructions may be encoded within memory 110 or memory 210. Memory 110 and memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Each of memory 110 and memory 210 may store timing intervals, counters, or other data used by control modules 106 and 206 to control the delivery of pacing pulses by pulse generators 102 and 202 to provide coordinated dual chamber pacing therapy.

Memory 210 may have a greater storage capacity than memory 110 in some examples. In order to reduce the overall size of pacemaker 10, and more specifically reduce the size of one of the capsules, one capsule 12 may be provided with a reduced storage capacity memory 110. Memory 110 may be used to store data used by control module 106 used on a frequent basis to control RA capsule operations. For example, data used by control module 106 for controlling pacing on a beat-by-beat basis may be stored in memory 110. Other data, such as EGM signal episode data, data stored for diagnostic purposes, may be transmitted from RA capsule 12 via electrical conductor to RV capsule 14 and stored in memory 210. Such data originating from RA capsule 12 may be retrieved from memory 210 for transmission to external device 20 by telemetry module 208. In this way, larger amounts of data, which may be stored for relatively long time, or data not needed by control module 106 for controlling RA capsule operations on a beat-by-beat basis may be stored in the larger capacity memory 210 allowing the overall size of RA capsule 12 to be reduced.

Pacemaker 10 may further include one or more physiological sensors 212 used for monitoring the patient, such as a pressure sensor, accelerometer, heart sound sensor, etc. In some examples, physiological sensors 212 include at least one physiological sensor producing a signal indicative of the metabolic demand of the patient. The signal indicative of the patient's metabolic demand is used by control module 206 for determining a sensor indicated pacing rate to control a pacing rate that meets the patient's metabolic demand. For example, sensors 212 may include an accelerometer for producing a patient activity signal, which may be passed to control module 206 and/or control module 106. In some examples, one control module 106 or 206 determines a sensor indicated pacing rate based on a sensor signal and transmits the sensor indicated pacing rate to the other control module 106 or 206 via electrical conductor 16 so that both control modules are controlling pacing rate in the same manner.

Power source 214 provides power to each of the other modules and components of pacemaker 10 as required. Power may be provided from power source 214 to RA capsule 12 via electrical conductor 16. Power source 214 may include one or more energy storage devices, such as one or more rechargeable or non-rechargeable batteries. The connections between power source 214 and other pacemaker modules and components are not shown in FIG. 6 for the sake of clarity. In some examples, a V+ power line 126 (FIG. 4) extends through electrical conductor 16 and is electrically coupled to power source 214 and to control module 106 for providing a V+ signal to control module 106.

Telemetry module 208 includes a transceiver and associated antenna for transferring and receiving data via a radio frequency (RF) communication link as described above. RF communication with external device 20 (FIG. 1), may occur in the Medical Implant Communication Service (MICS)

band, the Medical Data Service (MEDS) band, or other frequency bands, including, but not limited to a 2.4 GHz industrial, scientific and medical (ISM) band for Bluetooth and IEEE 802.11 b/g/n standards. Telemetry module 208 transmits data between external device 20 and RA capsule 12 via a data line 122 (shown in FIG. 5A) included in electrical conductor 16 in the example shown. Data line 122 extending through electrical conductor 16 provides data communication between control module 106 of RA capsule 12 and telemetry module 208.

In the example of FIG. 6, each capsule 12 and 14 performs pacing and sensing functions using separate pulse generators 102 and 202, sensing modules 104 and 204 and control modules 106 and 206. Shared telemetry functions with external device 20 via telemetry module 208, shared data storage in memory 210, and a shared power source 214 are enabled by electrical conductor 16 that includes a data line 122 and a power line 126. By separating some pacing and sensing functions across two separate capsules 12 and 14, each capsule can be reduced in overall size compared to a unitary pacemaker housing. By sharing some functions, such as wireless telemetry, data storage and/or power supply, one capsule 12 can be reduced in size compared to the other capsule 14.

Figure 7:
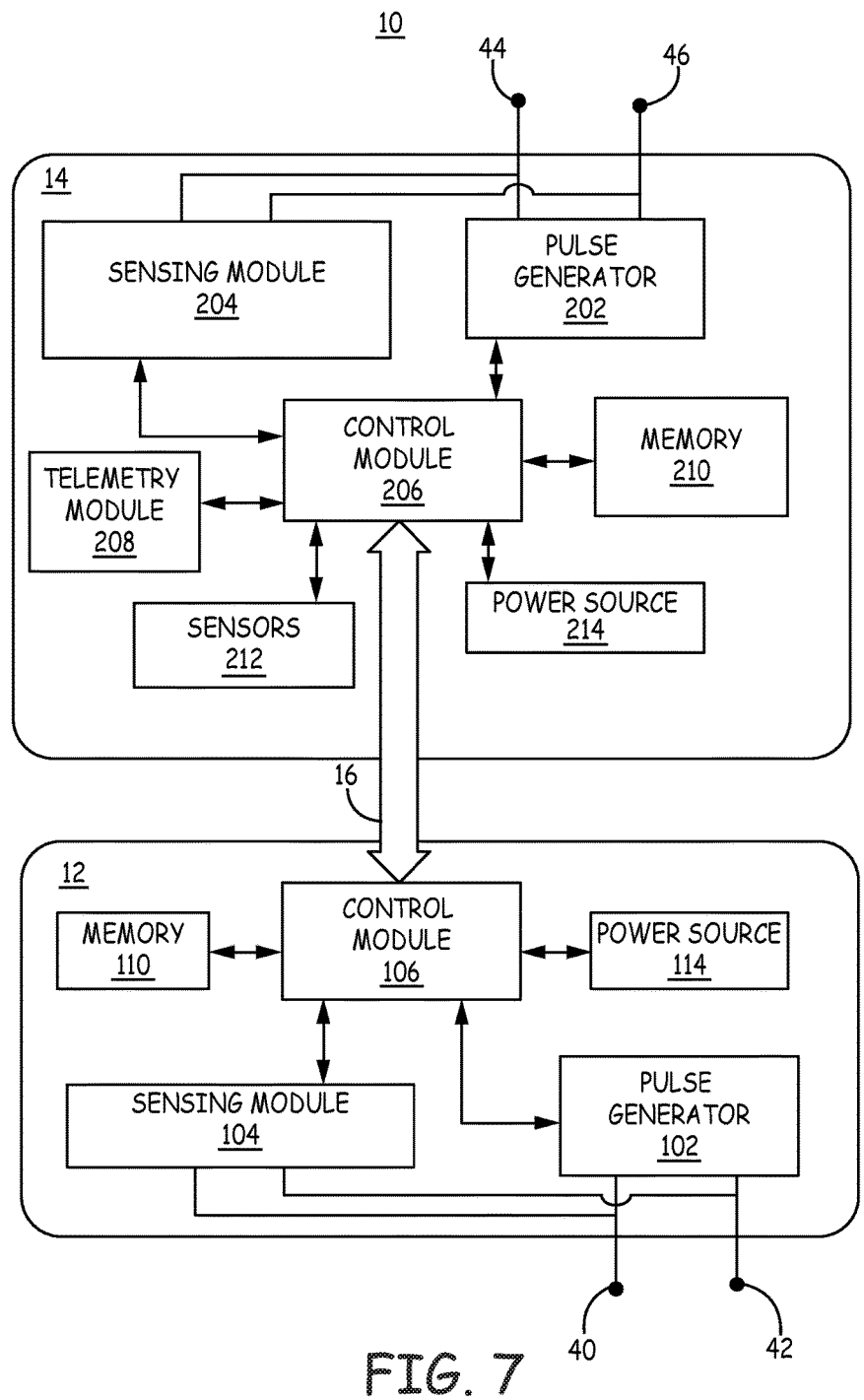
FIG. 7 is a functional block diagram of the pacemaker of FIG. 1 according to another example configuration.

FIG. 7 is a functional block diagram of pacemaker 10 according to another example. In FIG. 7, electrical conductor 16 that tethers capsules 12 and 14 together includes only a data line 122 (FIG. 5A) but no power line 126. RA capsule 12 includes a power source 114 for providing power to control module 106, pulse generator 102, sensing module 104 and memory 110. Electrical conductor 16 is used for data communication between RV capsule 14 and RA capsule 12 but not for power transfer.

Figure 8:
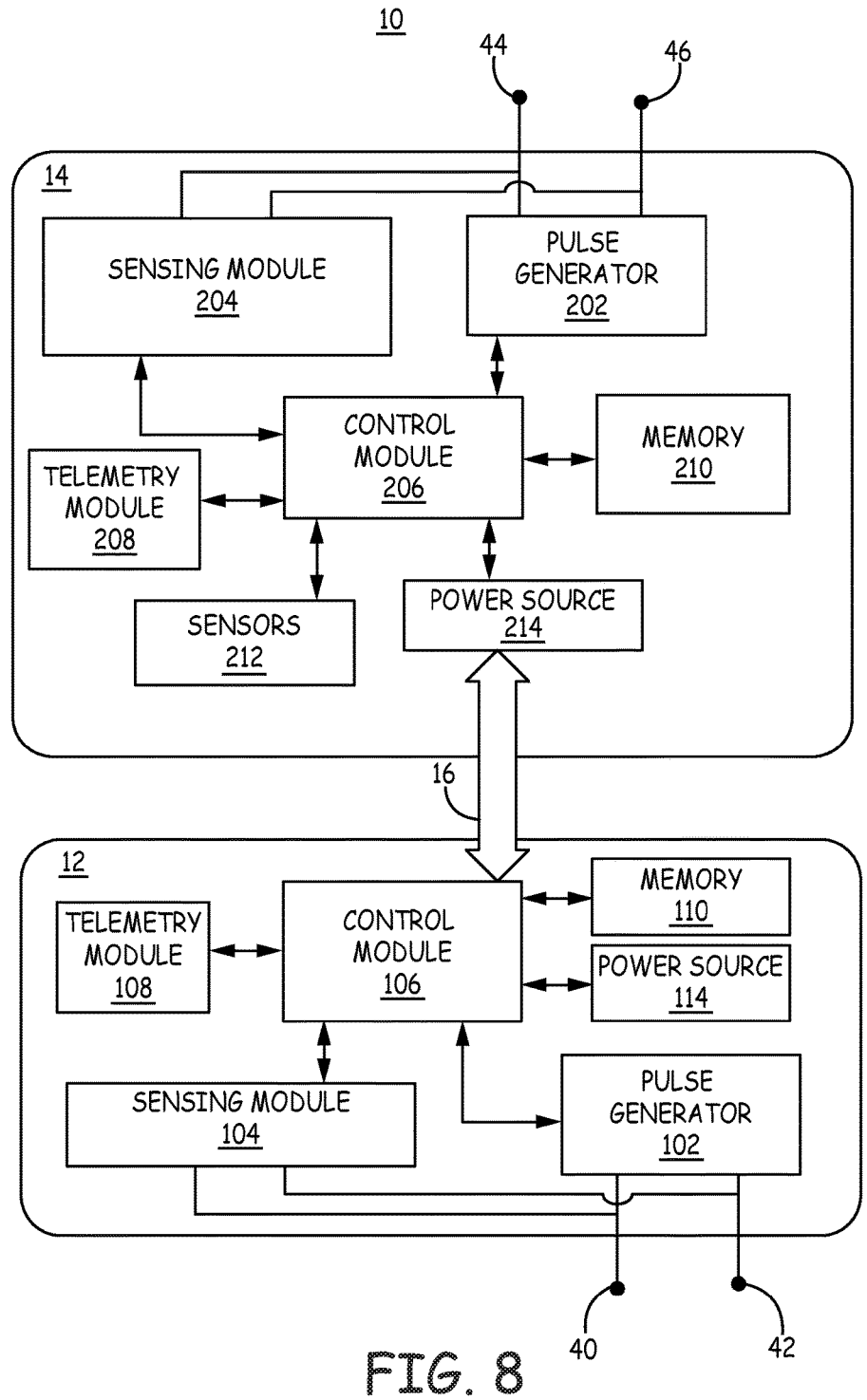
FIG. 8 is a functional block diagram of yet another example configuration of the pacemaker of FIG. 1.

FIG. 8 is a functional block diagram of yet another example configuration of pacemaker 10. In this configuration, RA capsule 12 includes a telemetry module 108 and memory 110 with sufficient storage capacity to support RA pacing and monitoring functions. In some examples RA capsule 12 does not include a power source, e.g., as shown in FIG. 6. Electrical conductor 16 includes a V+ signal line but does not include a separate data communication line. Electrical conductor 16 provides power from power source 214 of RV capsule 14 to RA capsule 12.

In other examples, RA capsule 12 includes a back-up power source 114 to provide power to pulse generator 102, sensing module 104, control module 106, memory 110, and telemetry module 108, if included. Power source 114 may have a much smaller capacity than power source 214 and provides back up power when a short circuit or open circuit condition is detected. If power is lost, back-up power source 114 is configured to provide power to the other modules and components of capsule 12 as needed. Control module 106 may operate in a power-savings mode, e.g., by reducing or disabling non-critical device functions.

Figure 9:
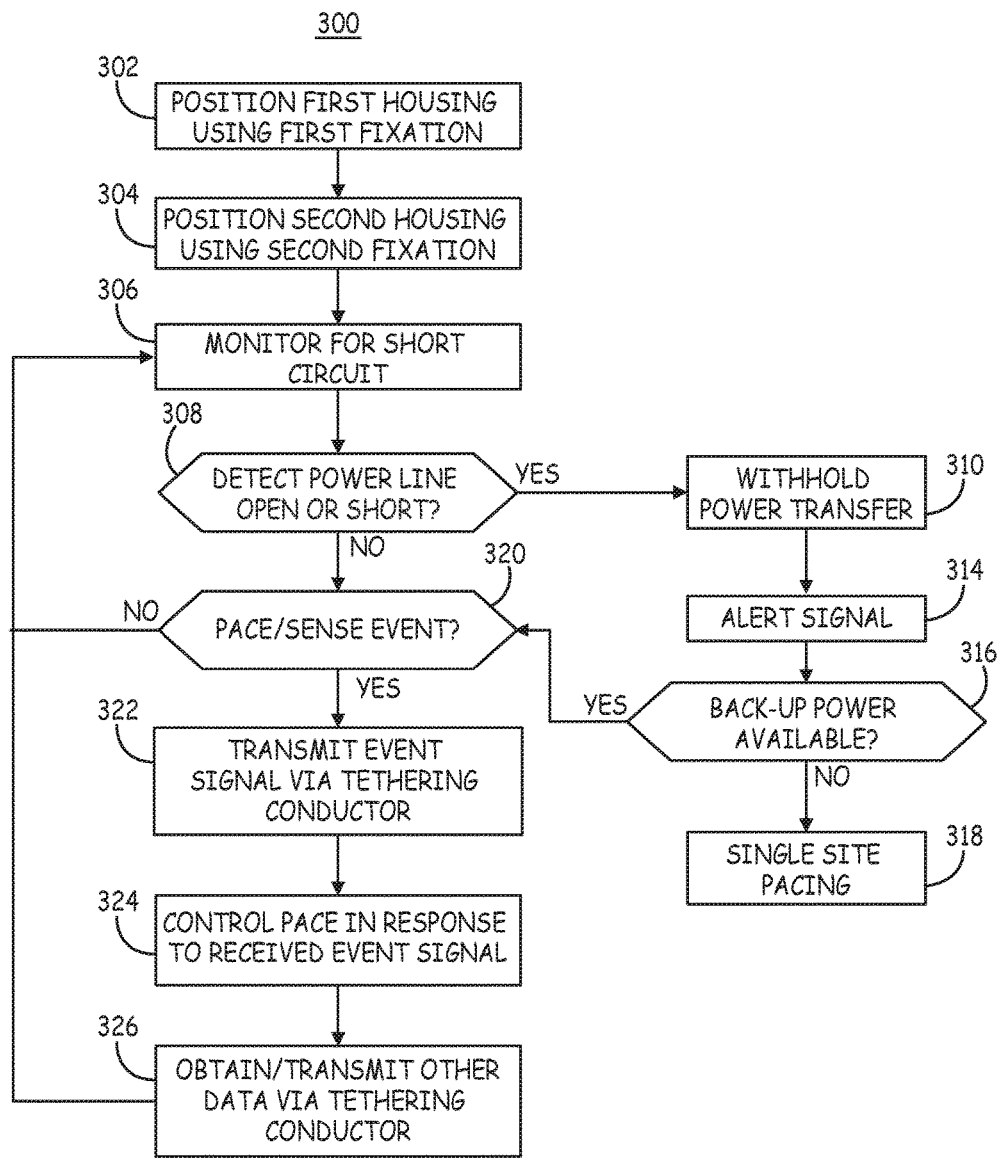
FIG. 9 is a flow chart of a method performed by the pacemaker of FIG. 1 according to one example.

FIG. 9 is a flow chart of a method performed by pacemaker 10 according to one example. At block 302, the implantable pacemaker 10 is advanced via a delivery tool, e.g., an elongated flexible catheter, to position the distal housing end 68 of capsule 14 at a first desired pacing site, e.g. in the right ventricle, and anchor electrode 44 at the desired pacing site using fixation member 32. Testing, such as pacing capture threshold, may be performed at block 302 to confirm that the implantation site is acceptable.

At block 304, the delivery tool is maneuvered to position distal housing end 58 of capsule 12 at a second desired pacing site, e.g. in the right atrium. It is contemplated that in some examples, capsules 12 and 14 may be positioned within or along the same heart chamber for pacing at multiple locations of the same heart chamber, e.g., the left ventricle. The tip electrode 40 is anchored at the second pacing site using fixation member 30, which may have a different fixation force than fixation member 32 as described previously herein. The two housings 50 and 60 may remain tethered together by elongated electrical conductor 16 throughout the implantation process, having a proximal end coupled to the capsule 12 and a distal end coupled to capsule 14. The two capsules 12 and 14 are positioned for delivering pacing pulses to the first pacing site via tip electrode 44 and ring electrode 46 and the second pacing site via tip electrode 40 and ring electrode 42. The electrical conductor 16 is used to transfer signals along a signal line extending through the elongated electrical conductor 16 between the first housing and the second housing to enable coordinated delivery of the first pacing pulses and the second pacing pulses in a dual chamber of multi-site pacing mode.

In various examples, the transferred signal enabling coordinated dual chamber or multi-site pacing by the two capsules 12 and 14 may include a V+ signal for power transfer to power a pulse generator enclosed by one of the housings 50 or 60 from a power source enclosed by the other one of the housings 50 or 60. If electrical conductor 16 includes a power line 126 (FIG. 5) for power transfer as shown in FIGS. 6 and 8, the control module 206 of capsule 14 may monitor for a short or open circuit of the power line 126 at block 304. Short circuit monitoring and open circuit monitoring may include monitoring the electrical current such that if a very high current (or low impedance) or very low current (or high impedance) is detected a short circuit (or open circuit) is detected. If a power line short is detected, at decision block 308, the power transfer is withheld at block 310 by control module 206. Control module 206 may generate an alert signal at block 314 that is transmitted via telemetry module 208 to external device 20 to notify the patient, a clinician or other user of the short circuit condition.

In some examples, capsule 12 may include a power source 114 that is a small capacity, back-up power source for use during a short circuit condition. Control module 106 may enable a power-savings operating mode that limits pacing at a base rate and/or reduces or eliminates non-critical device functions. When back-up power source 114 becomes the power source for capsule 12, a power-on reset condition may occur. In some examples, capsule 12 may transfer a signal via electrical conductor 16 to signal to capsule 14 that back-up power is available. In other examples, the pacemaker 10010 may be automatically configured to switch to a back-up power operation mode upon detecting a power line short or open circuit condition that includes withholding power transfer but allows the separately powered capsules to continue operating in a coordinated dual chamber or multi-site manner, which may involve transferring other data communication signals via a data line of electrical conductor 16 as described below. The process of flow chart 300 may advance to block 320 if back-up power is available. If back-up power is not available as determined at block 316, control module 206 may switch to a single chamber or single site pacing mode at block 318.

In other examples, the transferred signal enabling coordinated dual chamber or multi-site pacing by the two capsules 12 and 14 may include a pace delivery signal or a sensed event signal. At block 320, if a pacing pulse is delivered by the pulse generator 102 or 202 enclosed by one the housings 50 or 60, then a pace event signal is transferred at block 322 by the respective control module 106 or 206 that controlled the pacing pulse delivery, via a data line included in electrical conductor 16, to the other control module 106 or 206 enclosed by the other housing 50 or 60. Similarly if a cardiac event (e.g., a P-wave or R-wave) is sensed by one of the sensing modules 104 or 204 enclosed by one of the housings 50 or 60, the respective control module 106 or 206 enclosed by the same housing 50 or 60 transfers a sensed event signal via the electrical conductor 16 at block 322 to the other one of the control modules 106 or 206 enclosed by the other one of the housings 50 or 60.

At block 324, the pulse generator 102 or 202 enclosed by the other one of the housings 50 or 60 is controlled by the control module 106 or 206 that received the pace delivery signal or the sensed event signal via the electrical conductor 16. The pulse generator 102 or 202 may be controlled to inhibit a pacing pulse in response to a received pace delivery or sensed event signal or trigger a pacing pulse to be delivered at a programmed pacing escape interval following the received pace delivery signal or sensed event signal. The response of the control module 102 or 202 at block 324 to a received signal may depend upon which type of signal (pace delivery signal or sensed event signal) is received, a programmed pacing mode, and the timing of the received signal relative to a previous paced or sensed event.

In other examples, the transferred signal enabling coordinated dual chamber or multi-site pacing may include retrieving a sensing and/or pacing control parameter stored in a memory 110 or 210. As such, at block 326, other data may be transmitted between the capsules 12 and 14 via the electrical conductor 16 extending between the housings 50 and 60. For example, pacemaker 410 may be an interrupt-driven device that sends or retrieves data at block 326 upon interrupt clock signals. At block 326, data may be sent to or retrieved from memory 110 or 210 enclosed by one of the housings 50 or 60, respectively, by a control module 106 or 206 enclosed by the other one of the housings 50 or 60. Such data may include physiological data to be stored by the memory 110 or 210 of one capsule 12 or 14 or operating control parameters stored by the memory 110 or 210 of one capsule 12 or 14 and retrieved by the control module 106 or 206 of the other capsule 12 or 14, e.g., when the other capsule 12 or 14 has limited memory storage capacity compared to the first capsule.

Data obtained or transmitted at block 326 may include data transferred from control module 106 to telemetry module 208 via electrical conductor 16 or data received by telemetry module 208 from external device 20 transferred to control module 106. Such data may include operating control parameters required by control module 106 that enable coordinated dual chamber or multi-site pacing pulse delivery by the separate capsules 12 and 14.

If a short or open circuit condition has not been previously detected at block 308, the control module 206 may continue monitoring for a power line short at block 306 during pacing operations performed at blocks 320 through 326 as indicated by the return arrow to block 306. It is recognized that once a power line short or open circuit condition is detected at block 308, monitoring for a power line short circuit or open circuit and the responses at blocks 310 through 316 need not be repeated.

Thus, various examples of a pacemaker having two distinct housings tethered together by an electrical conductor have been described. It is recognized that various modifications may be made to the described embodiments without departing from the scope of the following claims.

The invention claimed is:
1. An implantable pacemaker, comprising:
a first housing enclosing a first pulse generator configured for delivering first pacing pulses to a first heart location via at least one first electrode carried by the first housing;
a second housing enclosing a second pulse generator configured for delivering second pacing pulses to a second heart location spaced apart from the first heart location via at least one second electrode carried by the second housing; and
an elongated electrical conductor having a proximal end and a distal end, the proximal end coupled to the first housing and the distal end coupled to the second housing to tether the first housing and the second housing together, the elongated electrical conductor comprising a signal line configured to carry an electrical signal between the first housing and the second housing,
the first housing comprising a first fixation feature configured to fix the first housing at the first heart location with a first fixation force that requires a first pulling force to dislodge the first housing from the first heart location;
the second housing comprising a second fixation feature configured to fix the second housing at the second heart location with a second fixation force that requires a second pulling force to dislodge the second housing from the second heart location, the second fixation force of the second fixation feature being less than the first fixation force of the first fixation feature so that the first pulling force required to dislodge the first housing is greater than the second pulling force required to dislodge the second housing to cause the second housing to preferentially dislodge from the second heart location instead of the first housing being dislodged from the first heart location in response to tensile forces along the elongated electrical conductor.

2. The pacemaker of claim 1, further comprising:
a first control module enclosed by the first housing;
a second control module enclosed by the second housing;
the signal line comprising a data line extending through the elongated electrical conductor, the first control module configured to send a communication data signal to the second control module via the data line.

3. The pacemaker of claim 1, further comprising:
a first control module and a first memory for storing data enclosed by the first housing;
a second control module enclosed by the second housing;
the signal line comprising a data line extending through the elongated electrical conductor, the second control module configured to access the first memory via the data line.

4. The pacemaker of claim 1, further comprising:
a power source enclosed by the first housing;
the signal line comprising a power signal line for transferring power from the power source to the second pulse generator.

5. The pacemaker of claim 4, further comprising:
a control module enclosed by the first housing and configured to:
test the power signal line for detecting whether one of a short circuit condition and an open circuit condition exists along the power line, and
withhold transferring power from the power source to the second pulse generator in response to detecting the one of the short circuit condition and the open circuit condition.

6. The pacemaker of claim 1, further comprising:
a telemetry module enclosed within the first housing and configured for wireless communication with an external device;
a control module enclosed within the second housing;
the signal line comprising a data line extending through the electrical conductor, the control module configured to send data to and receive data from the telemetry module via the data line.

7. The pacemaker of claim 1, further comprising:
a telemetry module enclosed within one of the first housing and the second housing and configured for wireless communication with an external device;
wherein the signal line comprises an antenna coupled to the telemetry module.

8. The pacemaker of claim 1, wherein the first housing comprises a longitudinal sidewall and the first fixation feature comprises a concavity in the longitudinal sidewall to promote the growth of encapsulating tissue toward a central axis of the first housing to increase the first pulling force required to dislodge the first housing after tissue encapsulation at the first heart location.

9. The pacemaker of claim 1, further comprising:
the first fixation feature comprising a first fixation member coupled to the first housing;
the second fixation feature comprising a second fixation member coupled to the second housing,
wherein the first fixation member comprises at least one of a first length, a first stiffness, a first thickness, and a first bending angle that is greater than a respective one of a second length, a second stiffness, a second thickness and a second bending angle of the second fixation member.

10. The pacemaker of claim 1, wherein the first fixation feature comprises an active fixation member and the second fixation feature comprises a passive fixation member.

11. The pacemaker of claim 1, wherein:
the first fixation feature comprises a first surface chemistry and a first surface geometry of the first housing,
the second fixation feature comprises a second surface chemistry and a second surface geometry of the second housing, at least one of the first surface chemistry being more hydrophobic than the second surface chemistry or the first surface geometry being less smooth than the second surface geometry so that at least one of the first surface chemistry and the first surface geometry contribute to at least one of a faster rate of tissue encapsulation of the first housing and a greater final thickness of tissue encapsulation of the first housing contributing to the greater first pulling force required to dislodge the first housing compared to a respective one of a rate of tissue encapsulation of the second housing and a final thickness of tissue encapsulation of the second housing after implantation of the pacemaker.

12. The pacemaker of claim 1, further comprising:
a first sensing module enclosed by the first housing;
a second sensing module enclosed by the second housing; and
a third electrode carried by the electrical conductor and coupled to one of the first sensing module and the second sensing module.

13. The pacemaker of claim 1, further comprising:
a first control module enclosed by the first housing and coupled to the first pulse generator for controlling the delivering of the first pacing pulses;
a second control module enclosed by the second housing and coupled to the second pulse generator;
the signal line comprising a data line for transmitting a pace delivery signal from the first control module to the second control module,
the second control module configured to control the delivering of the second pacing pulses by the second pulse generator in response to the pace delivery signal.

14. The pacemaker of claim 1, further comprising:
a first sensing module enclosed by the first housing and configured to sense a cardiac event signal via a pair of electrodes coupled to the pacemaker;
a first control module enclosed by the first housing and coupled to the first sensing module, the first control module configured to transmit a sensed event signal via the signal line;
a second control module enclosed by the second housing and coupled to the second pulse generator;
the second control module configured to receive the sensed event signal via the signal line and control the delivering of the second pacing pulses by the second pulse generator in response to the sensed event signal.

15. The pacemaker of claim 1, wherein:
the first housing comprises a proximal end, a distal end, and a longitudinal sidewall extending between the first housing proximal end and the first housing distal end;
the first fixation feature comprises a concavity extending circumferentially around the first housing along the longitudinal sidewall.

16. The pacemaker of claim 1, wherein the first housing has an outer surface defining a first surface chemistry and the second housing has an outer surface defining a second surface chemistry, wherein the second fixation feature comprises the second surface chemistry being more hydrophilic than the first surface chemistry.

17. The pacemaker of claim 16, further comprising at least one of a first coating covering at least a portion of the first housing and defining the first surface chemistry and/or a second coating covering at least a portion of the second housing and defining the second surface chemistry.

18. The pacemaker of claim 1, wherein the first housing has an outer surface defining a first surface geometry and the second housing has an outer surface defining a second surface geometry, the second fixation feature comprising the second surface geometry being smoother than the first surface geometry.

19. The pacemaker of claim 18, further comprising at least one of a first coating covering at least a portion of the first housing and defining the first surface geometry and/or a second coating covering at least a portion of the second housing and defining the second surface geometry.

20. The pacemaker of claim 1, further comprising an anti-inflammatory coating covering at least a portion of the second housing.

21. The pacemaker of claim 1, further comprising:
the signal line comprising a data line extending through the elongated electrical conductor;
a first sensing module enclosed by the first housing and configured to sense a cardiac event signal via at least the first electrode;
a first control module enclosed by the first housing and configured to transmit a sensed event signal via the data line in response to the first sensing module sensing the cardiac event signal;
a second control module enclosed by the second housing and configured to receive the sensed event signal and provide a response to the sensed event signal, the response comprising one of inhibiting the second pulse generator from delivering one of the second pacing pulses or controlling the second pulse generator to deliver one of the second pacing pulses at a pacing escape interval following the received sensed event signal.

22. The implantable pacemaker of claim 1, wherein the first heart location is a ventricular heart location and the second heart location is an atrial heart location, the first fixation feature being configured to fix the first housing at the ventricular heart location with the first fixation force, the second fixation feature being configured to fix the second housing at the atrial heart location with the second fixation force.

23. A non-transitory, computer-readable storage medium comprising a set of instructions which, when executed by a control module of an implantable pacemaker, cause the pacemaker to:

deliver first pacing pulses to a first heart location by a first pulse generator enclosed in a first housing via at least one first electrode carried by the first housing;

deliver second pacing pulses to a second heart location by a second pulse generator enclosed in a second housing via at least one second electrode carried by the second housing; and transfer a signal via an elongated electrical conductor extending from the first housing to the second housing, the transferred signal enabling coordinated delivery of the first pacing pulses and the second pacing pulses, wherein the first housing comprises a first fixation feature configured to fix the first housing at the first heart location with a first fixation force that requires a first pulling force to dislodge the first housing from the first heart location;

the second housing comprising a second fixation feature configured to fix the second housing at the second heart location with a second fixation force that requires a second pulling force to dislodge the second housing from the second heart location, the second fixation force of the second fixation feature being less than the first fixation force so that the first pulling force required to dislodge the first housing is greater than the second pulling force required to dislodge the second housing to cause the second housing to preferentially dislodge from the second heart location instead of the first housing being dislodged from the first heart location in response to tensile forces along the elongated electrical conductor.

* * * * *